(12) United States Patent
Muir

(10) Patent No.: US 7,691,794 B2
(45) Date of Patent: Apr. 6, 2010

(54) LUBRICATING OIL AND FUEL COMPOSITIONS

(75) Inventor: Ronald J. Muir, West Hill (CA)

(73) Assignee: Chemtura Corporation, Middlebury, CT (US)

( * ) Notice: Subject to any disclaimer, the term of this patent is extended or adjusted under 35 U.S.C. 154(b) by 1059 days.

(21) Appl. No.: 11/326,282

(22) Filed: Jan. 4, 2006

(65) Prior Publication Data
US 2007/0155631 A1 Jul. 5, 2007

(51) Int. Cl.
*C10M 163/00* (2006.01)
*C10L 1/22* (2006.01)
*C10M 139/00* (2006.01)
*C10M 133/00* (2006.01)

(52) U.S. Cl. ...................... 508/189; 508/190
(58) Field of Classification Search ............. 508/4, 508/121, 189, 154, 185, 190
See application file for complete search history.

(56) References Cited

U.S. PATENT DOCUMENTS

| | | |
|---|---|---|
| 2,933,520 A | 4/1960 | Bader |
| 3,038,935 A | 6/1962 | Gerber et al. |
| 3,133,944 A | 5/1964 | Christenson |
| 3,189,652 A | 6/1965 | Pollitzer |
| 3,239,463 A | 3/1966 | Knowles et al. |
| 3,446,808 A | 5/1969 | Cyba |
| 3,471,537 A | 10/1969 | Berke et al. |
| 3,505,226 A | 4/1970 | Cyba |
| 3,673,186 A | 6/1972 | Cyba |
| 3,692,680 A | 9/1972 | Cyba |
| 3,787,416 A | 1/1974 | Cyba |
| 3,914,182 A | 10/1975 | Ker et al. |
| 4,474,670 A | 10/1984 | Braid et al. |
| 4,529,528 A | 7/1985 | Horodysky |
| 4,533,481 A | 8/1985 | Jahnke |
| 4,539,126 A | 9/1985 | Bleeker et al. |
| 4,741,848 A | 5/1988 | Koch et al. |
| 4,828,733 A | 5/1989 | Faring et al. |
| 4,906,252 A | 3/1990 | Gutierrez et al. |
| 5,023,366 A | 6/1991 | Yamaguchi et al. |
| 5,110,488 A | 5/1992 | Tipton et al. |
| 5,281,346 A | 1/1994 | Adams et al. |
| 5,330,666 A * | 7/1994 | Habeeb ............ 508/518 |
| 5,336,278 A | 8/1994 | Adams et al. |
| 5,356,546 A | 10/1994 | Blystone et al. |
| 5,458,793 A | 10/1995 | Adams et al. |
| 5,498,809 A | 3/1996 | Emert et al. |
| 5,523,431 A * | 6/1996 | Skold ............ 554/70 |
| 5,688,751 A | 11/1997 | Cleveland et al. |
| 5,698,499 A | 12/1997 | Baranski et al. |
| 5,854,182 A | 12/1998 | Swami et al. |
| 5,900,392 A * | 5/1999 | Bernhard ............ 508/154 |
| 6,174,842 B1 | 1/2001 | Gatto et al. |
| 6,191,330 B1 * | 2/2001 | Matsuno et al. .......... 585/21 |
| 6,200,936 B1 | 3/2001 | Moreton |
| 6,242,393 B1 * | 6/2001 | Ishida et al. ............ 508/462 |
| 6,268,320 B1 | 7/2001 | Crawford |
| 6,310,011 B1 | 10/2001 | Karn et al. |
| 6,339,052 B1 | 1/2002 | Dohhen et al. |
| 6,355,074 B1 * | 3/2002 | Emert et al. ............ 44/317 |
| 2003/0000866 A1 | 1/2003 | Cain |
| 2004/0038834 A1 | 2/2004 | Gahagan |
| 2006/0276350 A1 | 12/2006 | Habeeb et al. |
| 2006/0281643 A1 | 12/2006 | Habeeb et al. |

FOREIGN PATENT DOCUMENTS

| | | |
|---|---|---|
| EP | 0949321 A2 | 10/1999 |
| JP | 08165484 A | 6/1996 |
| WO | WO2004104146 A1 | 12/2004 |
| WO | 2008016485 A1 | 2/2008 |

OTHER PUBLICATIONS

Lubrication and Lubricants, E.R. Braithwaite. Ed., Elsevier Co.(N.Y. 1967) Chapter 166-196, Synthetic Lubricants.
J.A. Walker et al., Characterization of Lubrication Oils by Differential Scanning. SAE Technical Paper Series, 801383, pp. 20-23. (1980).
USPTO Office Action mailed Sep. 15, 2008; U.S. Appl. No. 11/037,623; 11 Pgs.
Response filed Dec. 11, 2008, to USPTO Office Action mailed Sep. 15, 2008; U.S. Appl. No. 11/037,623; 18 Pgs.
USPTO Office Action mailed Apr. 2, 2009 ; U.S. Appl. No. 11/037,623; 23 Pgs.
USPTO Office Action mailed Apr. 28, 2009 ; U.S. Appl. No. 12/333,938; 32 Pgs.
USPTO Office Action mailed Apr. 2, 2009 ; U.S. Appl. No. 12/334,065; 25 Pgs.
USPTO Office Action mailed Apr. 2, 2009 ; U.S. Appl. No. 12/336,076; 28 Pgs.
USPTO Office Action mailed Mar. 17, 2009 ; U.S. Appl. No. 12/336,119; 15 Pgs.
USPTO Office Action mailed Apr. 29, 2008; U.S. Appl. No. 11/124,652; 10 Pgs.
Response filed Jul. 11, 2008, to USPTO Office Action mailed Apr. 29, 2008; U.S. Appl. No. 11/124,652; 13 Pgs.
USPTO Office Action mailed Oct. 17, 2008; U.S. Appl. No. 11/124,652; 8 Pgs.
Response filed Jan. 16, 2009; to USPTO Office Action mailed Oct. 17, 2008; U.S. Appl. No. 11/124,652; 13 Pgs.
USPTO Office Action mailed May 8, 2009 ; U.S. Appl. No. 11/124,652; 7 Pgs.

* cited by examiner

*Primary Examiner*—Glenn A Caldarola
*Assistant Examiner*—Pamela Weiss
(74) *Attorney, Agent, or Firm*—Katten Muchin Rosenman LLP

(57) ABSTRACT

Disclosed herein are reaction products of an acidic organic compound, a boron compound, and an alkoxylated amine and/or alkoxylated amide. Also disclosed are lubricating oil compositions and fuel compositions containing the reaction products.

10 Claims, No Drawings

LUBRICATING OIL AND FUEL COMPOSITIONS

BACKGROUND OF THE INVENTION

1. Field of the Invention

The present invention generally relates to a class of reduced ash detergent/anti-oxidant additives that are products of the reaction of acidic organic compounds, boron compounds, and alkoxylated amines and/or an alkoxylated amides useful as lubricating oil and fuel additives.

2. Description of Related Art

Metal detergents represent a major source of ash in formulated engine oils. Alkaline earth sulfonates, phenates and salicylates are typically used in modern engine oils to provide detergency and alkaline reserve. Detergents are necessary components of engine oils for both gasoline and diesel engines. Incomplete combustion of the fuel produces soot that can lead to sludge deposits, as well as carbon and varnish deposits. In the case of diesel fuel, residual sulfur in the fuel burns in the combustion chamber to produce sulfur derived acids. These acids produce corrosion and corrosive wear in the engine, and they also accelerate the degradation of the oil. Neutral and overbased detergents are introduced into engine oils to neutralize these acidic compounds, thereby preventing the formation of harmful engine deposits and dramatically increasing engine life.

U.S. Pat. No. 5,330,666 discloses a lubricant oil composition useful for reducing friction in an internal combustion engine which comprises a lubricating oil basestock and an alkoxylated amine salt of a hydrocarbylsalicylic acid of a defined formula.

U.S. Pat. No. 5,688,751 discloses that two-stroke cycle engines can be effectively lubricated by supplying to the engine a mixture of an oil of lubricating viscosity and a hydrocarbyl-substituted hydroxyaromatic carboxylic acid or an ester, unsubstituted amide, hydrocarbyl-substituted amide, ammonium salt, hydrocarbylamine salt, or monovalent metal salt thereof in an amount suitable to reduce piston deposits in said engine. The mixture supplied to the engine contains less than 0.06 percent by weight of divalent metals.

U.S. Pat. No. 5,854,182 discloses the preparation of magnesium borate overbased metallic detergent having magnesium borate uniformally dispersed in an extremely fine particle size by using magnesium alkoxide and boric acid. The preparation involves reacting a neutral sulphonate of an alkaline earth metal with magnesium alkoxide and boric acid under anhydrous conditions in the presence of a dilution solvent followed by distillation to remove alcohol and part of dilution solvent therefrom. The borated mixture is then cooled, filtered to recover magnesium borated metal detergent, which is said to exhibit excellent cleaning and dispersing performance, very good hydrolytic and oxidation stability, and good extreme pressure and antiwear properties.

U.S. Pat. No. 6,174,842 discloses a lubricating oil composition that contains from about 50 to 1000 parts per million of molybdenum from a molybdenum compound that is oil-soluble and substantially free of reactive sulfur, about 1,000 to 20,000 parts per million of a diarylamine, and about 2,000 to 40,000 parts per million of a phenate. This combination of ingredients is said to provide improved oxidation control and improved deposit control to the lubricating oil.

U.S. Pat. No. 6,339,052 discloses a lubricating oil composition for gasoline and diesel internal combustion engines includes a major portion of an oil of lubricating viscosity; from 0.1 to 20.0% w/w of a component A, which is a sulfurized, overbased calcium phenate detergent derived from distilled, hydrogenated cashew nut shell liquid; and from 0.1 to 10.0% w/w of a component B, which is an amine salt of phosphorodithioic acid of a specified formula derived from cashew nut shell liquid.

SUMMARY OF THE INVENTION

In accordance with one embodiment of the present invention, a metal-free detergent and antioxidant additive is provided comprising the reaction product of an acidic organic compound, a boron compound, and an alkoxylated amine and/or an alkoxylated amide.

In accordance with a second embodiment of the present invention, a process for preparing a metal-free detergent and antioxidant additive is provided, the process comprising reacting an acidic organic compound with a boron compound and an alkoxylated amine and/or an alkoxylated amide.

In accordance with a third embodiment of the present invention, a lubricating oil concentrate is provided comprising about 10 wt. % to about 90 wt. % of at least one reaction product of an acidic organic compound, a boron compound, and an alkoxylated amine and/or an alkoxylated amide; and about 90 wt. % to about 10 wt. % of an organic diluent.

In accordance with a fourth embodiment of the present invention, a lubricating oil composition is provided comprising (a) an oil of lubricating viscosity; and (b) an effective amount of at least one reaction product of an acidic organic compound, a boron compound, and an alkoxylated amine and/or an alkoxylated amide.

In accordance with a fifth embodiment of the present invention, a fuel concentrate is provided comprising a major amount of an inert stable oleophilic organic solvent boiling in the range of about 150° F. to about 400° F. and a minor effective amount of at least one reaction product of an acidic organic compound, a boron compound, and an alkoxylated amine and/or an alkoxylated amide.

In accordance with a sixth embodiment of the present invention, a fuel composition is provided comprising (a) a hydrocarbon fuel, and (b) an effective amount of at least one reaction product of an acidic organic compound, a boron compound, and an alkoxylated amine and/or an alkoxylated amide.

In accordance with a seventh embodiment of the present invention, a method for reducing the formation of deposits in an internal combustion engine is provided, the method comprising operating the engine with a lubricating oil composition is provided comprising (a) an oil of lubricating viscosity; and (b) a deposit-inhibiting effective amount of at least one reaction product of an acidic organic compound, a boron compound, and an alkoxylated amine and/or an alkoxylated amide.

The reaction products of the present invention advantageously provide improved detergency and oxidation stability. Furthermore, the reaction products provide excellent detergency and cleanliness to an oil of lubricating viscosity when evaluated using the panel coker test and excellent antioxidant performance when evaluated using pressure differential scanning calorimetry (PDSC). These reaction products are also useful when employed in fuels.

DESCRIPTION OF THE PREFERRED EMBODIMENTS

One aspect of the present invention is directed to reaction products of at least one or more acidic organic compounds, one or more boron compounds, and one or more alkoxylated amines and/or one or more alkoxylated amides, each of which are described hereinbelow.

The Acidic Organic Compounds

Suitable acidic organic compounds include, but are not limited to, alkyl substituted salicylic acids, di-substituted salicylic acids, oil soluble hydroxy carboxylic acids, salicylic acid calixarenes, sulfur-containing calixarenes, the acidic structures disclosed in U.S. Pat. Nos. 2,933,520; 3,038,935; 3,133,944; 3,471,537; 4,828,733; 6,310,011; 5,281,346; 5,336,278; 5,356,546; and 5,458,793 and the like and combinations thereof.

Useful substituted salicylic acids are either commercially available or may be prepared by methods known in the art, e.g., U.S. Pat. No. 5,023,366, and can be represented by the structure of formula I:

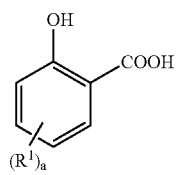

wherein $R^1$ is independently a hydrocarbyl group having from 1 to about 30 carbon atoms, and a is an integer of 1 or 2. The term "hydrocarbyl" includes hydrocarbon as well as substantially hydrocarbon groups. "Substantially hydrocarbon" describes groups that contain heteroatom substituents that do not alter the predominantly hydrocarbon nature of the group. Representative examples of hydrocarbyl groups for use herein include the following:

(1) hydrocarbon substituents, i.e., aliphatic (e.g., alkyl or alkenyl), alicyclic (e.g., cycloalkyl, cycloalkenyl) substituents, aromatic substituents, aromatic-, aliphatic-, and alicyclic-substituted aromatic substituents, and the like, as well as cyclic substituents wherein the ring is completed through another portion of the molecule (that is, for example, any two indicated substituents may together form an alicyclic radical);

(2) substituted hydrocarbon substituents, i.e., those substituents containing non-hydrocarbon groups which do not alter the predominantly hydrocarbon nature of the substituent, e.g., halo, hydroxy, mercapto, nitro, nitroso, sulfoxy, etc.; and (3) heteroatom substituents, i.e., substituents that will, while having a predominantly hydrocarbon character, contain an atom other than carbon present in a ring or chain otherwise composed of carbon atoms (e.g., alkoxy or alkylthio). Suitable heteroatoms will be apparent to those of ordinary skill in the art and include, for example, sulfur, oxygen, nitrogen, and such substituents as, e.g., pyridyl, furyl, thienyl, imidazolyl, etc. Preferably, no more than about 2, more preferably no more than one, hetero substituent will be present for every ten carbon atoms in the hydrocarbyl group. Most preferably, there will be no such heteroatom substituents in the hydrocarbyl group, i.e., the hydrocarbyl group is purely hydrocarbon.

Examples of $R^1$ in formula I above include, but are not limited to, unsubstituted phenyl;

phenyl substituted with one or more alkyl groups, e.g., methyl, ethyl, propyl, butyl, pentyl, hexyl, heptyl, octyl, nonyl, decyl, isomers of the foregoing, and the like; phenyl substituted with one or more alkoxy groups, such as methoxy, ethoxy, propoxy, butoxy, pentoxy, hexoxy, heptoxy, octoxy, nonoxy, decoxy, isomers of the foregoing, and the like;

phenyl substituted with one or more alkyl amino or aryl amino groups;

naphthyl and alkyl substituted naphthyl;

straight chain or branched chain alkyl or alkenyl groups containing from one to fifty carbon atoms, including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, oleyl, nonadecyl, eicosyl, heneicosyl, docosyl, tricosyl, tetracosyl, pentacosyl, triacontyl, pentatriacontyl, tetracontyl, pentacontyl, isomers of the foregoing, and the like; and cyclic alkyl groups, such as cyclopentyl, cyclohexyl, cycloheptyl, cyclooctyl, and cyclododecyl.

It will be noted that these salicylic acid derivatives can be either monosubstituted or disubstituted, i.e., when a in the formula equals 1 or 2, respectively.

Salicylic acid calixarenes such as those described in U.S. Pat. No. 6,200,936, the content of which is incorporated herein by reference, can be used as the acid compounds in the reaction products of the present invention. Such calixarenes include, but are not limited to, cyclic compounds comprising m units of a salicylic acid of formula IIa:

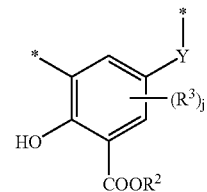

(IIa)

and n units of a phenol of formula IIb:

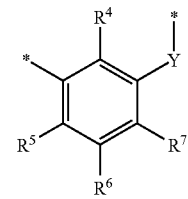

(IIb)

which are joined together to form a ring, wherein each Y is independently a divalent bridging group; $R^2$ is independently hydrogen or an alkyl group of 1 to 6 carbon atoms; $R^3$ is independently hydrogen or an alkyl group of 1 to 60 carbon atoms; and j is 1 or 2; either $R^4$ is hydroxy and $R^5$ and $R^7$ are independently hydrogen, hydrocarbyl or hetero-substituted hydrocarbyl, or $R^5$ and $R^7$ are hydroxyl and $R^4$ is either hydrogen, hydrocarbyl or hetero-substituted hydrocarbyl; $R^6$ is independently hydrogen, a hydrocarbyl or a hetero-substituted hydrocarbyl group; m is from 1 to 8; n is at least 3, and m+n is 4 to 20.

When more than one salicylic acid unit is present in the ring (i.e., m>1), the salicylic acid units (formula IIa) and phenol units (formula IIb) are distributed randomly, although this does not exclude the possibility that in some rings there may be several salicylic acid units joined together in a row.

Each Y may independently be represented by the formula $(CHR^8)_d$ in which $R^8$ is either hydrogen or hydrocarbyl and d is an integer which is at least 1. In one embodiment, $R^8$ contains 1 to 6 carbon atoms, and in one embodiment it is methyl. In another embodiment, d is from 1 to 4. Y may optionally be sulfur rather than $(CHR^8)_d$ in up to about 50% of the units, such that the amount of sulfur incorporated in the molecule is up to about 50 mole %. In one embodiment, the amount of sulfur is between about 8 and about 20 mole %. In another embodiment, the compound is sulfur-free. For convenience, these compounds are sometimes referred to as "salixarenes" and their metal salts as "salixarates".

In one embodiment, Y is $CH_2$; $R^4$ is hydroxyl; $R^5$ and $R^7$ are independently either hydrogen, hydrocarbyl or hetero-substituted hydrocarbyl; $R^6$ is either hydrocarbyl or hetero-substituted hydrocarbyl; $R^2$ is H; $R^3$ is an alkyl group of 6 to about 50 carbon atoms, preferably 4 to about 40 carbon atoms, more preferably 6 to about 25 carbon atoms; and m+n has a value of at least 5, preferably at least 6, and more preferably at least 8, wherein m is 1 or 2. Preferably, m is 1.

In another embodiment, $R^5$ and $R^7$ are hydrogen; $R^6$ is hydrocarbyl, preferably alkyl of greater than 4 carbon atoms, and more preferably greater than 9 carbon atoms; $R^3$ is hydrogen; m+n is from 6 to 12; and m is 1 or 2.

For a review of calixarenes, see, e.g., *Monographs in Supramolecular Chemistry* by C. David Gutsche, Series Editor-J. Fraser Stoddart, published by the Royal Society of Chemistry, 1989. Generally, calixarenes having a substituent hydroxyl group or groups include homocalixarenes, oxacalixarenes, homooxacalixarenes, and heterocalixarenes.

Sulfur-containing calixarenes, e.g., those described in U.S. Pat. No. 6,268,320, the contents of which is incorporated herein by reference in its entirety, can also be used as the acid compounds of the present invention. Such calixarenes include, but are not limited to, compounds represented by formula (III):

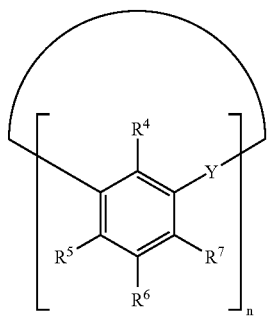

(III)

wherein Y is a divalent bridging group, at least one of said bridging groups being a sulfur atom; either $R^4$ is hydroxyl and $R^5$ and $R^7$ are independently either hydrogen or hydrocarbyl, or $R^5$ and $R^7$ are hydroxyl and $R^4$ is either hydrogen or hydrocarbyl; $R^6$ is hydrogen or a hydrocarbyl group; and n is a number having a value of at least 4.

In formula III, Y is a divalent bridging group or a sulfur atom with the proviso that at least one Y group is a sulfur atom. The divalent bridging group, when not a sulfur atom, can be a divalent hydrocarbon group or divalent hetero-substituted hydrocarbon group of 1 to 18 carbon atoms, and in a preferred embodiment, 1 to 6 carbon atoms. The heteroatoms can be —O—, —NH—, or —S—. The integer "n" is an integer that typically has a value of at least 4, preferably from 4 to 12, and more preferably, 4 to 8. In one embodiment, n-2 to n-6 of the Y groups are sulfur atoms. In another embodiment n-3 to n-10 of the Y groups are sulfur atoms. In yet another embodiment, one of the Y groups is a sulfur atom. Preferably, the amount of sulfur incorporated in the calixarene is between about 5 and about 50 mole %, such that between about 5 and about 50% of the groups Y in formula III are sulfur atoms. More preferably, the amount of sulfur is between about 8 and about 20 mole %.

In one embodiment, when Y of formula III is not a sulfur atom, it is a divalent group represented by the formula $(CHR^8)_d$ in which $R^8$ is either hydrogen or a hydrocarbyl group and d is an integer that is at least one. $R^8$ is preferably a hydrocarbyl group of 1 to about 18 carbon atoms, and more preferably, 1 to 6 carbon atoms. Representative examples of such hydrocarbyl groups include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, isomers or the foregoing, and the like. Preferably, d is from 1 to 3, more preferably 1 to 2, and most preferably, d is 1. As defined above, the term "hydrocarbyl groups" includes hetero-substituted hydrocarbyl groups, and are preferably those in which the heteroatom, e.g., —O—, —NH—, or —S—, interrupts a chain of carbon atoms; an example being an alkoxy-alkyl group of 2 to 20 carbons.

$R^6$ is hydrogen or can be a hydrocarbyl group which may be derived from a polyolefin such as a polyethylene, polypropylene, polybutylene, or polyisobutylene, or a polyolefin copolymer such as an ethylene/propylene copolymer. Other examples of $R^6$ include dodecyl, octadecyl and the like. Heteroatoms, if present, can again be —O—, —NH—, or —S—. These hydrocarbyl groups preferably have 1 to about 20 carbon atoms and more preferably, 1 to 6 carbon atoms.

Either $R^4$ is hydroxyl and $R^5$ and $R^7$ are independently either hydrogen or hydrocarbyl, or $R^5$ and $R^7$ are hydroxyl and $R^4$ is either hydrogen or hydrocarbyl. In one embodiment, $R^4$ is hydrogen, $R^5$ and $R^7$ are hydroxyl, and $R^6$ is either hydrogen or hydrocarbyl in the formula III and the calixarene is a resorcinarene. The hydrocarbyl groups preferably have 1 to about 24 carbon atoms, more preferably 1 to 12 carbon atoms. The heteroatoms, when present, can be —O—, —NH—, or —S—.

In one embodiment, Y is either sulfur or $(CR^9R^{10})_e$, where either one of $R^9$ and $R^{10}$ is hydrogen and the other is hydrogen or hydrocarbyl; $R^5$ and $R^7$ are independently either hydrogen or hydrocarbyl, $R^6$ is hydrocarbyl; n is 6; and e is at least 1, preferably 1 to 4, and more preferably, 1. Preferably, $R^5$ and $R^7$ are hydrogen and $R^6$ is hydrocarbyl, preferably alkyl of greater than 4, more preferably greater than 9, and most preferably greater than 12 carbon atoms; and one of $R^9$ or $R^{10}$ is hydrogen and the other is either hydrogen or alkyl, preferably hydrogen.

The foregoing sulfur-containing calixarenes typically have a molecular weight below about 1880. Preferably, the molecular weight of the sulfur-containing calixarene is from about 460 to about 1870, more preferably from about 460 to about 1800, and most preferably from about 460 to about 1750.

Acids described in U.S. Pat. Nos. 2,933,520; 3,038,935; 3,133,944; 3,471,537; 4,828,733; 5,281,346; 5,336,278; 5,356,546; 5,458,793; and 6,310,011, the contents of which are incorporated herein by reference in their entirety, can also be used as the acid compounds of the present invention. Examples of such acids include, but are not limited to, compounds of the formula:

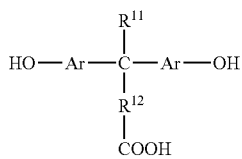

wherein $R^{11}$ is a hydrocarbon or halogen, $R^{12}$ is a hydrocarbon, and Ar is a substituted or unsubstituted aryl. Useful compounds similar to these include 3,5,3',5'-tetra-substituted 4,4'-dihydroxymethyl carboxylic acids and acids of the formula

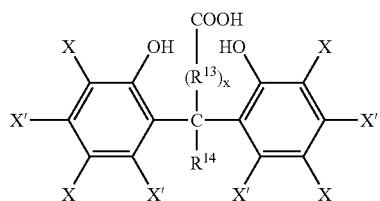

wherein X and X' are independently hydrogen, hydrocarbyl, and halogen, $R^{13}$ is polymethylene or branched or unbranched alkylene, x is 0 or 1 and $R^{14}$ is hydrogen or hydrocarbyl.

The acids and salts described in U.S. Pat. Nos. 5,281,346; 5,336,278; 5,356,546; 5,458,793; and 6,310,011 are similar to the above and are also contemplated for use in the practice of the present invention, as are those of the formula

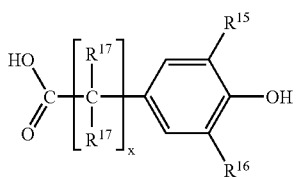

wherein $R^{15}$ and $R^{16}$ independently are hydrogen, a hydrocarbyl group containing 1 to about 18 carbon atoms, or tertiary alkyl or aralkyl groups containing 4 to 8 carbon atoms with the proviso that only one of $R^{15}$ and $R^{16}$ can be hydrogen; each $R^{17}$ independently are hydrogen, a hydrocarbyl group, aralkyl groups, and cycloalkyl groups, and x is 0 to 24.

Oil soluble hydroxy carboxylic acids including, but not limited to, 12-hydroxy stearic acid, alpha hydroxy carboxylic acids and the like can also be employed as the acidic compound of the present invention.

Preferably, the acidic organic compound is selected from the group consisting of alkyl substituted salicylic acids, di-substituted salicylic acids, oil soluble hydroxy carboxylic acids, salicylic acid calixarenes, sulfur-containing calixarenes, and the acidic structures disclosed in U.S. Pat. Nos. 2,933,520; 3,038,935; 3,133,944; 3,471,537; 4,828,733; 5,281,346; 5,336,278; 5,356,546; 5,458,793 and 6,310,011.

The Boron Compounds

The boron compound can be, for example, boric acid, a trialkyl borate in which the alkyl groups preferably comprise from 1 to 4 carbon atoms each, alkyl boric acid, dialkyl boric acid, boric oxide, boric acid complex, cycloalkyl boric acid, aryl boric acid, dicycloalkyl boric acid, diaryl boric acid, or substitution products of these with alkoxy, alkyl, and/or alkyl groups, and the like. Preferably, the boron compound of boric acid.

Alkoxylated Amines and/or Alkoxylated Amides

The alkoxylated amines or amides for use herein can include saturated or unsaturated mono or polyalkoxylated alkylamines or alkyl amides, e.g., dialkoxylated alkyl amines, saturated or unsaturated mono or polyalkoxylated arylamines or aryl amides and the like and mixtures thereof. As one skilled in the art will readily appreciate, the alkoxylated amines or amides for use herein can be obtained from primary, secondary or tertiary amines. The term "monoalkoxylated" as used herein shall be understood to mean an alkoxy unit attached via an oxygen linkage to the rest of the molecule wherein the alkoxy unit can contain 1 to about 60 alkoxy radicals, preferably from 1 to about 30 alkoxy radicals and more preferably from 1 to about 20 alkoxy radicals, in random or block sequences, and wherein each alkoxy radical can be the same or different, e.g., ethylene oxide-propylene oxide-ethylene oxide unit, ethylene oxide-ethylene oxide-ethylene oxide unit and the like. The term "polyalkoxylated" as used herein shall be understood to mean more than one alkoxy unit, e.g., a dialkoxylated unit, each attached via an oxygen linkage to the rest of the molecule wherein each alkoxy unit can contain 1 to about 60 alkoxy radicals, preferably from 1 to about 30 alkoxy radicals and more preferably from 1 to about 20 alkoxy radicals, in random or block sequences, and wherein each alkoxy radical can be the same or different as described hereinabove.

In one embodiment, the alkoxylated amines include, but are not limited to, mono or polyethoxylated amines or amides, mono or polyethoxylated fatty acid amines or fatty acid amides and the like and mixtures thereof.

In another embodiment, the alkoxylated amine or amide includes an alkoxylated derivative of an alkanolamine, e.g., diethanolamine or of triethanolamine, or alkanolamide, or an alkoxylated derivative of a reaction product of an alkanolamine or alkanolamide with a $C_4$-$C_{75}$ fatty acid ester. The fatty acid ester for use in forming the reaction product herein can be, for example, glycerol fatty acid esters, i.e., glycerides derived from natural sources such as, for example, beef tallow oil, lard oil, palm oil, castor oil, cottonseed oil, corn oil, peanut oil, soybean oil, sunflower oil, olive oil, whale oil, menhaden oil, sardine oil, coconut oil, palm kernel oil, babassu oil, rape oil, soya oil and the like with coconut oil being preferred for use herein.

The glycerol fatty acid esters will contain from about $C_4$ to about $C_{75}$ and preferably contain about $C_6$ to about $C_{24}$ fatty acid esters, i.e., several fatty acid moieties, the number and type varying with the source of the oil. Fatty acids are a class of compounds containing a long hydrocarbon chain and a terminal carboxylate group and are characterized as unsaturated or saturated depending upon whether a double bond is present in the hydrocarbon chain. Therefore, an unsaturated fatty acid has at least one double bond in its hydrocarbon chain whereas a saturated fatty acid has no double bonds in its fatty acid chain. Preferably, the acid is saturated. Examples of unsaturated fatty acids include, myristoleic acid, palmitoleic acid, oleic acid, linolenic acid, and the like. Examples of saturated fatty acids include caproic acid, caprylic acid, capric acid, lauric acid, myristic acid, palmitic acid, stearic acid, arachidic acid, behenic acid, lignoceric acid, and the like.

Representative examples of suitable alkoxylated amines include:

(a) an alkoxylated amine represented by general formula:

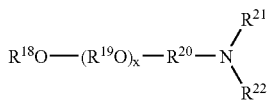

wherein $R^{18}$ is hydrogen or a substituted or unsubstituted hydrocarbyl having from 1 to about 30 carbon atoms and preferably from about 8 to about 30 carbon atoms; $R^{19}$ in each of the x ($R^{19}$O) groups is independently a straight or branched $C_2$-$C_4$ alkylene; $R^{20}$ is a bond or a substituted or unsubstituted hydrocarbylene having from 2 to about 6 carbon atoms; $R^{21}$ and $R^{22}$ are each independently hydrogen, substituted or unsubstituted hydrocarbyl having from 1 to about 30 carbon atoms, —$(R^{23})_n$—$(R^{19}O)_y R^{24}$, or $R^{21}$ and $R^{22}$ together with the nitrogen atom to which they are bonded are joined together to form a heterocyclic group; $R^{23}$ is substituted or unsubstituted hydrocarbylene containing from 1 to about 6 carbon atoms, $R^{24}$ is hydrogen or a linear or branched alkyl group having 1 to about 4 carbon atoms, n is 0 or 1, and x is an average number from 1 to about 60, preferably from 1 to about 30 and more preferably from 1 to about 20. Suitable hydrocarbyl (hydrocarbylene) groups include, but are not limited to, linear or branched alkyl (alkylene), linear or branched alkenyl (alkenylene), linear or branched alkynyl (alkynylene), aryl (arylene), aralkyl (aralkylene) groups and the like. Preferably, $R^{18}$ is a linear or branched alkyl or linear or branched alkenyl group having from about 8 to about 25 carbon atoms, $R^{19}$ in each of the x ($R^{19}$O) groups is independently a straight or branched $C_2$-$C_4$ alkylene, $R^{21}$ and $R^{22}$ are each independently hydrogen or a linear or branched alkyl group having from 1 to about 6 carbon atoms, and x is an average number from 1 to about 30.

(b) an alkoxylated amine represented by general formula:

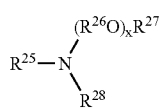

wherein $R^{25}$ is a substituted or unsubstituted hydrocarbyl having from 1 to about 30 carbon atoms and preferably from about 8 to about 30 carbon atoms; $R^{26}$ in each of the x ($R^{26}$O) groups is independently a straight or branched $C_2$-$C_4$ alkylene; $R^{27}$ is hydrogen or a straight or branched alkyl group having from 1 to about 6 carbon atoms; $R^{28}$ is a substituted or unsubstituted hydrocarbyl having from 1 to about 30 carbon atoms, e.g., a linear or branched alkynyl, aryl, or aralkyl group having from 1 to about 30 carbon atoms, and x is an average number from 1 to about 60. Preferably, $R^{25}$ is a straight or branched alkyl, straight or branched alkenyl, straight or branched alkynyl, aryl, or aralkyl groups.

(c) a dialkoxylated amine represented by general formula:

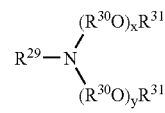

wherein $R^{29}$ is a linear or branched alkyl, linear or branched alkenyl, linear or branched alkynyl, aryl, or aralkyl group having from about 6 to about 30 carbon atoms, $R^{30}$ in each of the x ($R^{30}$O) and the y ($R^{30}$O) groups is independently a straight or branched $C_2$-$C_4$ alkylene, $R^{31}$ is independently hydrogen, or a linear or branched alkyl group having from 1 to about 4 carbon atoms and x and y are independently an average number from 1 to about 40. Preferably, $R^{29}$ is a straight or branched alkyl or straight or branched alkenyl group having from about 8 to about 30 carbon atoms, $R^{30}$ in each of the x ($R^{30}$O) and the y ($R^{30}$O) groups is independently a straight or branched $C_2$-$C_4$ alkylene, $R^{31}$ is independently hydrogen, methyl or ethyl, and x and y are independently an average number from 1 to about 20. More preferably, $R^{29}$ is a linear or branched alkyl group having from about 8 to about 25 carbon atoms, $R^{30}$ in each of the x ($R^{30}$O) and the y ($R^{30}$O) groups is independently ethylene or propylene, $R^{31}$ is independently hydrogen or methyl, and x and y are independently an average number from 1 to about 10. Even more preferably, $R^{29}$ is a linear or branched alkyl group having from about 8 to about 22 carbon atoms, $R^{30}$ in each of the x ($R^{30}$O) and the y ($R^{30}$O) groups is independently ethylene or propylene, $R^{31}$ is independently hydrogen or methyl, and x and y are independently an average number from 1 to about 5.

Preferred commercially available alkoxylated amines include those available from Akzo Nobel under the Ethomeen tradename, e.g., Ethomeen C/12, C/15, C/20, C/25, SV/12, SV/15, T/12, T/15, T/20 and T/25. Preferred commercially available alkoxylated amides include those available from Akzo Nobel under the Amadol tradename, e.g., Amadol CMA-2, Amadol CMA-5, Amadol OMA-2, Amadol OMA-3 and Amadol OMA-4.

In general, the reaction of the boron compound with the acidic compound and alkoxylated amine and/or alkoxylated amide of the present invention can be effected in any suitable manner. For example, the reaction can be conducted by first combining the acidic compound and boron compound in the desired ratio and in the presence of a suitable solvent, e.g., naphtha and polar solvents such as water and methanol. After a sufficient time, the boron compound dissolves whereupon the alkoxylated amine and/or alkoxylated amide is added slowly to effect neutralization and formation of desired reaction product. If desired, a diluting oil can be added as needed to control viscosity, particularly during removal of solvents by distillation. The reaction can typically be conducted by maintaining the reactants at a temperature of from about 20° C. to about 100° C. and preferably from about 50° C. to about 75° C. for a time period ranging from about 1 to about 4 hours.

If desired, the reaction can be carried out in an alcohol, e.g., aliphatic and aromatic alcohols, or a mercaptan, e.g., aliphatic and aromatic mercaptans, can be included in the reaction charge. Suitable aliphatic alcohols include, but are not limited to, methanol, ethanol, propanol, butanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, isomers thereof, and the like. Suitable aromatic alcohols include, but are not limited to, phenol, cresol, xylenol, and the like. The alcohol or aromatic phenol moiety may be substituted with alkoxy groups or thioalkoxy groups. Suitable mercaptans include, but are not limited to, butyl mercaptan, pentyl mercaptan, hexyl mercaptan, heptyl mercaptan, octyl mercaptan, nonyl mercaptan, decyl mercaptan, undecyl mercaptan, dodecyl mercaptan, and the like, as well as thiophenol, thiocresol, thioxylenol, and the like.

It will be understood by those skilled in the art that the foregoing reaction product will contain a complex mixture of compounds. The reaction product mixture need not be separated to isolate one or more specific components. Accordingly, the reaction product mixture can be employed as is in the lubrication oil composition or fuel composition of the present invention.

Lubricating Oil Compositions

The reaction products of the present invention are useful as additives in lubricating oil compositions. Generally, the lubricating oil compositions of this invention include as a first component an oil of lubricating viscosity. The oil of lubricating viscosity for use herein can be any presently known or later-discovered oil of lubricating viscosity used in formulating lubricating oil compositions for any and all such applications, e.g., engine oils, marine cylinder oils, functional fluids such as hydraulic oils, gear oils, transmission fluids, e.g., automatic transmission fluids, etc., turbine lubricants, trunk piston engine oils, compressor lubricants, metal-working lubricants, and other lubricating oil and grease compositions. Additionally, the oil of lubricating viscosity for use herein can optionally contain viscosity index improvers, e.g., polymeric alkylmethacrylates; olefinic copolymers, e.g., an ethylene-propylene copolymer or a styrene-butadiene copolymer; and the like and mixtures thereof.

As one skilled in the art would readily appreciate, the viscosity of the oil of lubricating viscosity is dependent upon the application. Accordingly, the viscosity of an oil of lubricating viscosity for use herein will ordinarily range from about 2 to about 2000 centistokes (cSt) at 100° Centigrade (C). Generally, individually the oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W; 10W-20, 10W-30, 10W-40, 10W-50, 15W, 15W-20, 15W-30 or 15W-40. Oils used as gear oils can have viscosities ranging from about 2 cSt to about 2000 cSt at 100° C.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fisher-Tropsch process. For example, a suitable oil of lubricating viscosity is one that comprises little, if any, heavy fraction; e.g., little, if any, lube oil fraction of viscosity about 20 cSt or higher at 100° C.

The oil of lubricating viscosity may be derived from natural lubricating oils, synthetic lubricating oils or mixtures thereof. Suitable oils includes base stocks obtained by isomerization of synthetic wax and slack wax, as well as hydrocracked base stocks produced by hydrocracking (rather than solvent extracting) the aromatic and polar components of the crude. Suitable oils include those in all API categories I, II, III, IV and V as defined in API Publication 1509, 14th Edition, Addendum I, December 1998. Group IV base oils are polyalphaolefins (PAO). Group V base oils include all other base oils not included in Group I, II, III, or IV. Although Group II, III and IV base oils are preferred for use in this invention, these preferred base oils may be prepared by combining one or more of Group I, II, III, IV and V base stocks or base oils.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils include, but are not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of about 1,000, diphenyl ether of polyethylene glycol having a molecular weight of about 500 to about 1000, diethyl ether of polypropylene glycol having a molecular weight of about 1,000 to about 1,500, etc.) or mono- and polycarboxylic esters thereof such as, for example, the acetic esters, mixed $C_3$-$C_8$ fatty acid esters, or the $C_{13}$oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl)silicate, tetra-(4-methyl-hexyl)silicate, tetra-(p-tertbutylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphionic acid, etc., polymeric tetrahydrofurans and the like.

The oil of lubricating viscosity may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

The oil of lubricating viscosity for use in the lubricating oil compositions may be present in a major amount, e.g., an amount of greater than 50 wt. %, preferably greater than about 70 wt. %, more preferably from about 80 to about 99.5 wt. % and most preferably from about 85 to about 98 wt. %, based on the total weight of the composition.

The reaction products of the present invention for use in the lubricating oil compositions of this invention can be used as a complete or partial replacement for commercially available antioxidants and detergents currently used in lubricant formulations and can be in combination with other additives typically found in motor oils. Generally, the reaction products of the present invention will be present in the lubricating oil compositions in an effective amount ranging from about 0.1 to about 15 wt. %, preferably from about 0.1 wt. % to about 10% wt. % and more preferably from about 0.5 wt. % to about 5 wt. %, based on the total weight of the lubricating oil composition.

If desired, other additives can be admixed with the foregoing lubricating oil compositions to enhance performance. When used in combination with other types of antioxidants or additives used in oil formulations, synergistic and/or additive performance effects may be obtained with respect to improved antioxidancy, antiwear, frictional and detergency and high temperature engine deposit properties. Such other additives can be any presently known or later-discovered additives used in formulating lubricating oil compositions. The lubricating oil additives typically found in lubricating oils are, for example, dispersants, detergents, corrosion/rust inhibitors, antioxidants, anti-wear agents, anti-foamants, friction modifiers, seal swell agents, emulsifiers, VI improvers, pour point depressants, and the like. See, for example, U.S. Pat. No. 5,498,809 for a description of useful lubricating oil composition additives, the disclosure of which is incorporated herein by reference in its entirety. The additives can be employed in the lubricating oil compositions at the usual levels in accordance with well known practice.

Examples of dispersants include polyisobutylene succinimides, polyisobutylene succinate esters, Mannich Base ashless dispersants, and the like. Examples of detergents include metallic and ashless alkyl phenates, metallic and ashless sulfurized alkyl phenates, metallic and ashless alkyl sulfonates, metallic and ashless alkyl salicylates, metallic and ashless saligenin derivatives, and the like.

Examples of other antioxidants include alkylated diphenylamines, N-alkylated phenylenediamines, phenyl-naphthylamine, alkylated phenyl-naphthylamine, dimethyl quinolines, trimethyldihydroquinolines and oligomeric compositions derived therefrom, hindered phenolics, alkylated hydroquinones, hydroxylated thiodiphenyl ethers, alkylidenebisphenols, thiopropionates, metallic dithiocarbamates, 1,3,4-dimercaptothiadiazole and derivatives, oil soluble copper compounds, and the like. Representative examples of such additives are those commercially available from such sources as Chemtura Corporation and include, for example, Naugalube® 438, Naugalube 438L, Naugalube 640, Naugalube 635, Naugalube 680, Naugalube AMS, Naugalube APAN, Naugard PANA, Naugalube TMQ, Naugalube 531, Naugalube 431, Naugard® BHT, Naugalube 403, Naugalube 420 and the like.

Examples of anti-wear additives that can be used in combination with the additives of the present invention include organo borates, organo phosphites, organo phosphates, organic sulfur-containing compounds, sulfurized olefins, sulfurized fatty acid derivatives (esters), chlorinated paraffins, zinc dialkyldithiophosphates, zinc diaryldithiophosphates, dialkyldithiophosphate esters, diaryl dithiophosphate esters, phosphosulfurized hydrocarbons, and the like. Representative examples of such additives are those commercially available from The Lubrizol Corporation such as Lubrizol 677A, Lubrizol 1095, Lubrizol 1097, Lubrizol 1360, Lubrizol 1395, Lubrizol 5139, Lubrizol 5604 and the like, and from Ciba Corporation such as Irgalube 353 and the like.

Examples of friction modifiers include fatty acid esters and amides, organo molybdenum compounds, molybdenum dialkyldithiocarbamates, molybdenum dialkyl dithiophosphates, molybdenum disulfide, tri-molybdenum cluster dialkyldithiocarbamates, non-sulfur molybdenum compounds and the like. Representative examples of such friction modifiers are those commercially available from R. T. Vanderbilt Company, Inc. such as Molyvan A, Molyvan L, Molyvan 807, Molyvan 856B, Molyvan 822, Molyvan 855, and the like; Asahi Denka Kogyo K.K. such as SAKURA-LUBE 100, SAKURA-LUBE 165, SAKURA-LUBE 300, SAKURA-LUBE 310G, SAKURA-LUBE 321, SAKURA-LUBE 474, SAKURA-LUBE 600, SAKURA-LUBE 700, and the like; and from Akzo Nobel Chemicals GmbH such as Ketjen-Ox 77M, Ketjen-Ox 77TS, and the like.

An example of an anti-foam agent is polysiloxane, and the like. Examples of rust inhibitors are polyoxyalkylene polyol, benzotriazole derivatives, and the like. Examples of VI improvers include olefin copolymers and dispersant olefin copolymers, and the like. An example of a pour point depressant is polymethacrylate, and the like.

As noted above, suitable anti-wear compounds include dihydrocarbyl dithiophosphates. Preferably, the hydrocarbyl groups contain an average of at least 3 carbon atoms. Particularly useful are metal salts of at least one dihydrocarbyl dithiophosphoric acid wherein the hydrocarbyl groups contain an average of at least 3 carbon atoms. The acids from which the dihydrocarbyl dithiophosphates can be derived can be illustrated by acids of the formula:

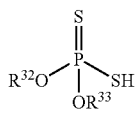

wherein $R^{32}$ and $R^{33}$ are the same or different and can be linear or branched alkyl, cycloalkyl, aralkyl, alkaryl, or substituted substantially hydrocarbyl radical derivatives of any of the above groups, and wherein the $R^{32}$ and $R^{33}$ groups in the acid each have, on average, at least 3 carbon atoms. By "substantially hydrocarbyl" is meant radicals containing substituent groups, e.g., 1 to 4 substituent groups per radical moiety such as, for example, ether, ester, thio, nitro, or halogen, that do not materially affect the hydrocarbon character of the radical.

Specific examples of suitable $R^{32}$ and $R^{33}$ radicals include isopropyl, isobutyl, n-butyl, sec-butyl, n-hexyl, heptyl, 2-ethylhexyl, diisobutyl, isooctyl, decyl, dodecyl, tetradecyl, hexadecyl, octadecyl, butylphenyl, o,p-dipentylphenyl, octylphenyl, polyisobutene-(molecular weight 350)-substituted phenyl, tetrapropylene-substituted phenyl, beta-octylbutylnaphthyl, cyclopentyl, cyclohexyl, phenyl, chlorophenyl, o-dichlorophenyl, bromophenyl, naphthenyl, 2-methylcyclohexyl, benzyl, chlorobenzyl, chloropentyl, dichlorophenyl, nitrophenyl, dichlorodecyl and xenyl radicals. Alkyl radicals having from about 3 to about 30 carbon atoms and aryl radicals having from about 6 to about 30 carbon atoms are preferred. Particularly preferred $R^{32}$ and $R^{33}$ radicals are alkyl of from 4 to about 18 carbon atoms.

The phosphorodithioic acids are readily obtainable by the reaction of a phosphorus pentasulfide and an aliphatic alcohol and/or phenol. The reaction involves at least mixing, at a temperature ranging from about 20° C. to about 200° C., about 4 moles of the alcohol or phenol with one mole of phosphorus pentasulfide. Hydrogen sulfide can be liberated as the reaction takes place. Mixtures of alcohols, phenols, or both can be employed, e.g., mixtures of $C_3$ to $C_{30}$ alcohols, $C_6$ to $C_{30}$ aromatic alcohols, etc. The metals useful to make the phosphate salts include, but are not limited to, Group I metals, Group II metals, aluminum, lead, tin, molybdenum, manganese, cobalt, and nickel with zinc being the preferred metal. Examples of metal compounds that can be reacted with the acid include lithium oxide, lithium hydroxide, lithium carbonate, lithium pentylate, sodium oxide, sodium hydroxide, sodium carbonate, sodium methylate, sodium propylate, sodium phenoxide, potassium oxide, potassium hydroxide, potassium carbonate, potassium methylate, silver oxide, silver carbonate, magnesium oxide, magnesium hydroxide, magnesium carbonate, magnesium ethylate, magnesium propylate, magnesium phenoxide, calcium oxide, calcium hydroxide, calcium carbonate, calcium methylate, calcium propylate, calcium pentylate, zinc oxide, zinc hydroxide, zinc carbonate, zinc propylate, strontium oxide, strontium hydroxide, cadmium oxide, cadmium hydroxide, cadmium carbonate, cadmium ethylate, barium oxide, barium hydroxide, barium hydrate, barium carbonate, barium ethylate, barium pentylate, aluminum oxide, aluminum propylate, lead oxide, lead hydroxide, lead carbonate, tin oxide, tin butylate, cobalt oxide, cobalt hydroxide, cobalt carbonate, cobalt pentylate, nickel oxide, nickel hydroxide, nickel carbonate and the like and mixtures thereof.

In some instances, the incorporation of certain ingredients, particularly carboxylic acids or metal carboxylates, e.g., small amounts of the metal acetate or acetic acid, used in conjunction with the metal reactant will facilitate the reaction and result in an improved product. For example, the use of up to about 5% of zinc acetate in combination with the required amount of zinc oxide facilitates the formation of a zinc phosphorodithioate.

The preparation of metal phosphorodithioates is well known in the art. See, e.g., U.S. Pat. Nos. 3,293,181; 3,397,145; 3,396,109; and 3,442,804; the disclosures of which are hereby incorporated by reference. Also useful as anti-wear additives are amine derivatives of dithiophosphoric acid compounds, such as are described in U.S. Pat. No. 3,637,499, the disclosure of which is hereby incorporated by reference in its entirety.

The zinc salts are most commonly used as anti-wear additives in lubricating oils in amounts ranging from about 0.1 to about 10 wt. %, preferably about 0.2 to about 2 wt. %, based upon the total weight of the lubricating oil composition. They may be prepared in accordance with known techniques, e.g., by first forming a dithiophosphoric acid, usually by reaction of an alcohol and/or a phenol with $P_2S_5$ and then neutralizing the dithiophosphoric acid with a suitable zinc compound.

Mixtures of alcohols can be used, including mixtures of primary and secondary alcohols, secondary generally for imparting improved antiwear properties and primary for thermal stability. In general, any basic or neutral zinc compound could be used, but the oxides, hydroxides, and carbonates are most generally employed. Commercial additives frequently contain an excess of zinc owing to use of an excess of the basic zinc compound in the neutralization reaction.

The zinc dihydrocarbyl dithiophosphates (ZDDP) are oil soluble salts of dihydrocarbyl esters of dithiophosphoric acids and can be represented by the following formula:

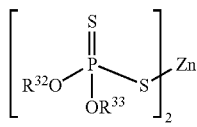

wherein $R^{32}$ and $R^{33}$ have the aforestated meanings.

The lubricating oil compositions of the present invention, when they contain these additives, are typically blended into a base oil in amounts such that the additives therein are effective to provide their normal attendant functions. Representative effective amounts of such additives are illustrated in Table 1.

TABLE 1

| Additives | Preferred Weight % | More Preferred Weight % |
|---|---|---|
| V.I. Improver | about 1 to about 12 | about 1 to about 4 |
| Corrosion Inhibitor | about 0.01 to about 3 | about 0.01 to about 1.5 |
| Oxidation Inhibitor | about 0.01 to about 5 | about 0.01 to about 1.5 |
| Dispersant | about 0.1 to about 10 | about 0.1 to about 5 |
| Lube Oil Flow Improver | about 0.01 to about 2 | about 0.01 to about 1.5 |
| Detergent/Rust Inhibitor | about 0.01 to about 6 | about 0.01 to about 3 |
| Pour Point Depressant | about 0.01 to about 1.5 | about 0.01 to about 0.5 |
| Anti-foaming Agents | about 0.001 to about 0.1 | about 0.001 to about 0.01 |
| Anti-wear Agents | about 0.001 to about 5 | about 0.001 to about 1.5 |
| Seal Swell Agents | about 0.1 to about 8 | about 0.1 to about 4 |
| Friction Modifiers | about 0.01 to about 3 | about 0.01 to about 1.5 |
| Lubricating Base Oil | Balance | Balance |

When other additives are employed, it may be desirable, although not necessary, to prepare additive concentrates comprising concentrated solutions or dispersions of one or more of the reaction products of the present invention, together with one or more other additives whereby several additives can be added simultaneously to the base oil to form the lubricating oil composition. Dissolution of the additive concentrate into the lubricating oil can be facilitated by, for example, solvents and by mixing accompanied by mild heating, but this is not essential.

The concentrate or additive-package will typically be formulated to contain the additives in proper amounts to provide the desired concentration in the final formulation when the additive-package is combined with a predetermined amount of base lubricant. Thus, the subject additives of the present invention can be added to small amounts of base oil or other compatible solvents along with other desirable additives to form additive-packages containing active ingredients in collective amounts of, typically, from about 2.5 to about 90 percent, preferably from about 15 to about 75 percent, and more preferably from about 25 percent to about 60 percent by weight additives in the appropriate proportions with the remainder being base oil. The final formulations can typically employ about 1 to 20 weight percent of the additive-package with the remainder being base oil.

All of the weight percentages expressed herein (unless otherwise indicated) are based on the active ingredient (AI) content of the additive, and/or upon the total weight of any additive-package, or formulation, which will be the sum of the AI weight of each additive plus the weight of total oil or diluent.

In general, the lubricating oil compositions of the present invention can contain the additives in a concentration ranging from about 0.05 to about 30 weight percent. A concentration range for the additives ranging from about 0.1 to about 10 weight percent based on the total weight of the oil composition is preferred. A more preferred concentration range is from about 0.2 to about 5 weight percent. In one embodiment, oil concentrates of the additives can contain from about 1 to about 75 weight percent of the additive in a carrier or diluent oil of lubricating oil viscosity.

The present invention advantageously provides the lubricating oil compositions containing the reaction products of this invention as an additive which provides deposit protection in addition to oxidation-corrosion protection. The lubricating oil compositions can also provide such protection while having relatively low levels of phosphorous, e.g., less than about 0.1%, preferably less than about 0.08% and more preferably less than about 0.05% by weight. Accordingly, the lubricating oil compositions of the present invention can be more environmentally desirable than the higher phosphorous lubricating oil compositions generally used in internal combustion engines because they facilitate longer catalytic converter life and activity while also providing the desired high deposit protection. This is due to the substantial absence of additives containing phosphorus compounds in these lubricating oil compositions. The reaction product for use herein may also protect against oxidation both in the presence of transition metals such as, for example, iron (Fe) and copper (Cu), etc., as well as in a metal free environment.

Fuel Compositions

The reaction products of the present invention are also useful as an additive for fuel compositions, e.g., as a friction modifier.

The fuel can be any fuel, e.g., motor fuels such as diesel fuel and gasoline, kerosene, jet fuels, alcoholic fuels such as methanol or ethanol; marine bunker fuel, natural gas, home heating fuel or a mixture of any of the foregoing. When the fuel is diesel, such fuel generally boils above about 212° F. The diesel fuel can comprise atmospheric distillate or vacuum distillate, or a blend in any proportion of straight run and thermally and/or catalytically cracked distillates. Preferred diesel fuels have a cetane number of at least 40, preferably above 45, and more preferably above 50. The diesel fuel can have such cetane numbers prior to the addition of any cetane improver. The cetane number of the fuel can be raised by the addition of a cetane improver.

When the fuel is gasoline, it can be derived from straight-chain naphtha, polymer gasoline, natural gasoline, catalytically cracked or thermally cracked hydrocarbons, catalytically reformed stocks, etc. It will be understood by one skilled in the art that gasoline fuels typically boil in the range of about 80°-450° F. and can contain straight chain or branched chain paraffins, cycloparaffins, olefins, aromatic hydrocarbons, and any mixture of these.

Generally, the composition of the fuel is not critical and any conventional motor fuel base can be employed in the practice of this invention.

The proper concentration of the reaction products of the present invention that are necessary to achieve the desired result, e.g., friction modification, in fuel compositions is dependent upon a variety of factors including, for example, the type of fuel used, the presence of other additives, etc. Generally, however, the additive concentration of the reaction product of this invention in the base fuel can range from about 10 to about 5,000 parts per million and preferably from about 50 to about 1,000 parts per million of the additive per part of base fuel. If other friction modifiers are present, a lesser amount of the reaction product of the present invention may be used.

If desired, one or more additional fuel additives may be incorporated into the fuel composition of the present invention. Such additives for use in the fuel additive and fuel compositions herein can be any presently known or later-discovered additive used in formulating fuel compositions. The fuel additives include, but are not limited to, detergents, cetane improvers, octane improvers, emission reducers, antioxidants, carrier fluids, metal deactivators, lead scavengers, rust inhibitors, bacteriostatic agents, corrosion inhibitors, antistatic additives, drag reducing agents, demulsifiers, dehazers, anti-icing additives, dispersants, combustion improvers and the like and mixtures thereof. A variety of the additives are known and commercially available. These additives, or their analogous compounds, can be employed for the preparation of the various fuel compositions herein. The additives may be employed in the fuel compositions at the usual levels in accordance with well known practice.

The additives described herein may also be formulated as a fuel concentrate, using an inert stable oleophilic organic solvent boiling in the range of about 150° F. to about 400° F. An aliphatic or an aromatic hydrocarbon solvent is preferred, e.g., solvents such as benzene, toluene, xylene or higher-boiling aromatics or aromatic thinners. Aliphatic alcohols of about 3 to 8 carbon atoms, e.g., isopropanol, isobutylcarbinol, n-butanol and the like, in combination with hydrocarbon solvents are also suitable for use with the fuel additive. In the fuel concentrate, the amount of the additive will be ordinarily be about 5 or more wt. % and generally not exceed about 70 wt. %, preferably from about 5 wt. % to about 50 wt. % and more preferably from about 10 wt. % to about 25 wt. %, based on the total weight of the fuel composition.

Examples of detergents include, but are not limited to, nitrogen-containing detergents such as, for example, aliphatic hydrocarbyl amines, hydrocarbyl-substituted poly (oxyalkylene)amines, hydrocarbyl-substituted succinimides, Mannich reaction products, nitro and amino aromatic esters of polyalkylphenoxyalkanols, polyalkylphenoxyaminoalkanes and post-treated derivatives of the foregoing nitrogen-containing compounds and the like and mixtures thereof.

Useful aliphatic hydrocarbyl-substituted amines which may be employed in the present invention are typically straight or branched chain hydrocarbyl-substituted amines having at least one basic nitrogen atom and wherein the hydrocarbyl group has a number average molecular weight of about 700 to about 3,000. Preferred aliphatic hydrocarbyl-substituted amines include polyisobutenyl and polyisobutyl monoamines and polyamines. The aliphatic hydrocarbyl amines employed in this invention are prepared by conventional procedures known in the art. Such aliphatic hydrocarbyl amines and their preparations are described in detail in U.S. Pat. Nos. 3,438,757; 3,565,804; 3,574,576; 3,848,056; 3,960,515; 4,832,702; and 6,203,584, the contents of each of which are incorporated by reference herein.

Useful hydrocarbyl-substituted poly(oxyalkylene)amines (also referred to as polyether amines) are generally hydrocarbyl-substituted poly(oxyalkylene)amines, e.g., hydrocarbyl poly(oxyalkylene)monoamines and polyamines wherein the hydrocarbyl group contains from 1 to about 30 carbon atoms, the number of oxyalkylene units range from about 5 to about 100, and the amine moiety is derived from ammonia, a primary alkyl or secondary dialkyl monoamine, or a polyamine having a terminal amino nitrogen atom. Preferably, the oxyalkylene moiety will be oxypropylene or oxybutylene or a mixture thereof. Such hydrocarbyl-substituted poly(oxyalkylene)amines are described, for example, in U.S. Pat. Nos. 5,112,364 and 6,217,624, the contents of which are incorporated by reference herein. A preferred type of hydrocarbyl-substituted poly(oxyalkylene)monoamine is an alkylphenyl poly(oxyalkylene)monoamine wherein the poly(oxyalkylene)moiety contains oxypropylene units or oxybutylene units or mixtures of oxypropylene and oxybutylene units.

An additional type of hydrocarbyl-substituted poly(oxyalkylene)amine are hydrocarbyl-substituted poly(oxyalkylene)aminocarbamates as disclosed, for example, in U.S. Pat. Nos. 4,160,648; 4,191,537; 4,197,409; 4,233,168; 4,236,020; 4,243,798; 4,270,930; 4,288,612 and 4,881,945, the contents of each of which are incorporated by reference herein. These hydrocarbyl poly(oxyalkylene)aminocarbamates contain at least one basic nitrogen atom and have an average molecular weight of about 500 to about 10,000, preferably about 500 to about 5,000, and more preferably about 1,000 to about 3,000. A preferred aminocarbamate is alkylphenyl poly(oxybutylene)aminocarbamate wherein the amine moiety is derived from ethylene diamine or diethylene triamine.

Useful hydrocarbyl-substituted succinimides are generally hydrocarbyl-substituted succinimides, e.g., polyalkyl and polyalkenyl succinimides wherein the polyalkyl or polyalkenyl group has an average molecular weight of about 500 to about 5,000, and preferably about 700 to about 3,000. The hydrocarbyl-substituted succinimides are typically prepared by reacting a hydrocarbyl-substituted succinic anhydride with an amine or polyamine having at least one reactive hydrogen bonded to an amine nitrogen atom. Preferred hydrocarbyl-substituted succinimides include polyisobutenyl and polyisobutanyl succinimides, and derivatives thereof. Examples of hydrocarbyl-substituted succinimides are described, for example, in U.S. Pat. Nos. 5,393,309; 5,588,973; 5,620,486; 5,916,825; 5,954,843; 5,993,497; and 6,114,542, and British Patent No. 1,486,144, the contents of each of which are incorporated by reference herein.

Useful Mannich reaction products are generally obtained from the Mannich condensation of a high molecular weight alkyl-substituted hydroxyaromatic compound, an amine containing at least one reactive hydrogen, and an aldehyde. The high molecular weight alkyl-substituted hydroxyaromatic compounds are preferably polyalkylphenols, e.g., polypropylphenol and polybutylphenol, wherein the polyalkyl group has an average molecular weight of about 600 to about 3,000. The amine reactant is typically a polyamine, such as alkylene polyamines, especially ethylene or polyethylene polyamines, for example, ethylene diamine, diethylene triamine, triethylene tetramine, and the like. The aldehyde reactant is generally an aliphatic aldehyde, such as formaldehyde, including paraformaldehyde and formalin, and acetaldehyde. A preferred Mannich reaction product is obtained by condensing a polyisobutylphenol with formaldehyde and diethylene triamine, wherein the polyisobutyl group has an average molecular weight of about 1,000. Examples of Mannich reaction products are described, for example, in U.S. Pat. Nos. 4,231,759 and 5,697,988, the contents of each of which are incorporated by reference herein.

Additional examples of the foregoing additives are described, for example, in U.S. Pat. Nos. 6,203,584; 6,616,776; 6,651,604 and 6,652,667, the contents of each of which are incorporated by reference herein.

Examples of antioxidants include, but are not limited to, aminic types, e.g., diphenylamine, phenyl-alpha-napthyl-amine, N,N-di(alkylphenyl)amines; and alkylated phenylene-diamines; phenolics such as, for example, BHT, sterically hindered alkyl phenols such as 2,6-di-tert-butylphenol, 2,6-di-tert-butyl-p-cresol and 2,6-di-tert-butyl-4-(2-octyl-3-propanoic)phenol and the like and mixtures thereof.

Examples of rust inhibitors include, but are not limited to, nonionic polyoxyalkylene agents, e.g., polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate; stearic acid and other fatty acids; dicarboxylic acids; fatty acid amine salts; partial carboxylic acid ester of polyhydric alcohol; (short-chain) alkenyl succinic acids; partial esters thereof and nitrogen-containing derivatives thereof and the like and mixtures thereof.

Examples of friction modifiers include, but are not limited to, borated fatty epoxides; fatty phosphites, fatty epoxides, glycerol esters, borated glycerol esters; and fatty imidazolines as disclosed in U.S. Pat. No. 6,372,696, the contents of which are incorporated by reference herein; and the like and mixtures thereof.

Examples of antifoaming agents include, but are not limited to, polymers of alkyl methacrylate; polymers of dimethylsilicone and the like and mixtures thereof.

Examples of dispersants include, but are not limited to, polyalkylene succinic anhydrides; non-nitrogen containing derivatives of a polyalkylene succinic anhydride; a basic nitrogen compound selected from the group consisting of succinimides, carboxylic acid amides, hydrocarbyl monoamines, hydrocarbyl polyamines, Mannich bases, copolymers which contain a carboxylate ester with one or more additional polar function, including amine, amide, imine, imide, hydroxyl, carboxyl, and the like, e.g., products prepared by copolymerization of long chain alkyl acrylates or methacrylates with monomers of the above function; and the like and mixtures thereof. The derivatives of these dispersants may also be used. Preferably, the dispersants are polyalkylene succinimides derived from animation of polyalkylene succinic anhydrides with polyalkylene polyamine.

The following non-limiting examples are illustrative of the present invention.

Example 1

To a small flask equipped with mechanical stirrer and condenser was added 94 grams of naphtha diluted alkyl salicylic acid (that contains 40 grams of actual alkyl salicylic acid). Next, 20 grams of methanol and 20 grams of isopropyl alcohol were added followed by 10 grams of boric acid. The mixture was heated to 70° C. and 36 grams of Ethomeen SV/15 (an ethoxylated(5)soyaalkylamine) available from AKZO Nobel (Chicago, Ill.) was added. The reaction mixture was heated slowly to 220° C. to remove volatiles and a clear brown viscous liquid was recovered that had a total base number (TBN) of 49.

Example 2

To a small flask equipped with mechanical stirrer and condenser was added 94 grams of alkyl salicylic acid (containing 40 grams of alkyl salicylic acid and 54 grams of naphtha solvent). Next, 10 grams of boric acid was added followed by 20 grams of methanol and 20 grams of iso propyl alcohol. The mixture was heated to 70° C. when 45 grams of monoethanolamide ethoxylate was added. The reaction mixture was heated to 210° C. over one hour to complete the reaction and the volatiles were removed leaving a clear brown liquid.

Example 3

Preparation of a Lubricating Oil Composition

To a SAE 50 base oil was blended 2 percent of the reaction product of Example 1.

Example 4

Preparation of a Lubricating Oil Composition

To a Castrol Magnatec GTX baseline engine oil was blended 5 percent of the reaction product of Example 1.

Comparative Example A

A quantity of 40 grams of alkyl ($C_{14}$-$C_{18}$) salicylic acid was added to a small reaction flask equipped with a mechanical stirrer and a condenser. Fifty grams of naphtha was added along with 40 grams of base oil, 15 grams of water and 30 grams of methanol. Mixing was started, 15 grams of boric acid was added, and then the mixture was heated to 70° C. At that temperature, 48.5 grams of a hydroxy ethyl alkyl imidazoline was added and the reaction temperature was increased slowly to 210° C. to remove volatiles. A clear brown viscous liquid was recovered that had a total alkalinity value of 46.

Comparative Example B

Preparation of a Lubricating Oil Composition

To a SAE 50 base oil was blended 5 percent of the reaction product of Comparative Example A.

Pressure Differential Scanning Calorimetry

The sample of Example 1 was subjected to PDSC testing and found to have an induction time of >180 minutes at 165° C. when the test was stopped.

Comparative Example C

Comparative Example A was repeated except that the alkyl imidazoline used was an amino ethyl alkyl imidazoline. The final product was a fluid hazy liquid with poor oil solubility.

Comparative Example D

Comparative Example A was repeated but the boric acid was not added. The final product was fluid, bright and clear.

Comparative Example E

In this example, the alkyl salicylic acid of Comparative Example A was replaced with an alkyl aromatic sulfonic acid. The product recovered was clear.

Comparative Example F

Preparation of a Lubricating Oil Composition

A lubricating oil composition was formed from Castrol Magnatec GTX baseline engine oil with no reaction product of Example 1.

Testing

To demonstrate the effectiveness of the additives of Example 1 and Comparative Example A of the present invention, each of the lubricating oil compositions of Example 3 and Comparative Example B and the additives of Example 2 and Comparative Examples D and E were evaluated using a Panel Coker test, each of the additives of Example 1 and Comparative Examples A and E were evaluated using the a Pressurized Differential Scanning Calorimetry (PDSC) test and the lubricating oil compositions of Example 4 and Comparative Example F were evaluated using a Thermo-Oxidation Engine Oil Simulation Test (TEOST) as described below.

Detergency Performance

Panel Coker Test

The detergency efficacy of crankcase oils can be assessed in terms of deposit forming tendency on a rectangular Al-steel panel in a Panel Coker test. In this test, 200 ml of the test sample is taken in sump and heated at 100° C. For a period of 6 hours, this heated oil is splashed by whiskers on the Al-steel panel, the temperature of which is maintained at 310° C. After completion of the test, any deposits on the panel are weighed. A decrease in the weight of deposits as compared with a similar composition lacking the detergent additive indicates improved detergency. The results of this test are set forth below in Table 2.

TABLE 2

Panel Coker Test Results

| Ex./Comp. Ex. | mg deposits |
|---|---|
| Example 2 | 12 |
| Example 3 | 5 |
| Comp. Ex. B | 6.5 |
| Comp. Ex. D | 150 |
| Comp. Ex. E | 243 |

Antioxidant Performance

Pressure Differential Scanning Calorimetry (PDSC)

PDSC (DuPont Model-910/1090B) can be used for relative antioxidant performance evaluation of the composition. In this method, a test sample (10 mg) taken in a sample boat is subjected to heating from 100-300° C. at the rate of 10° C. per minute under 500 psi oxygen pressure. The onset of oxidation temperature is adopted as a criterion for assessment of antioxidant performance. In general, an increase in onset of oxidation temperature indicates improvement in antioxidant performance. See J. A. Walker and W. Tsang, "Characterization of Lubrication Oils by Differential Scanning Calorimetry", SAE Technical Paper Series, 801383 (Oct. 20-23, 1980). The results of this test are set forth below in Table 3.

TABLE 3

PDSC Test Results

| Ex./Comp. Ex. | Time (minutes) |
|---|---|
| Example 1 | 342 |
| Comp. Ex. A | >180 |
| Comp. Ex. E | 34.8 |

Mid-High Temperature Thermo-Oxidative Engine Oil Simulation Test

The Mid-High Temperature Thermo-oxidative Engine Oil Simulation Test (MHT TEOST) was performed to determine the deposit forming tendencies of the motor engine oil. The improved thermal deposit control of the additives of this invention in stabilizing the engine oil formulation has been clearly demonstrated by the MHT TEOST. This test determines the mass of deposit formed on a specially constructed steel rod by continuously stressing a repetitive passage of 8.5 ml of test oil under thermal-oxidative and catalytic conditions. The instrument used was manufactured by Tannas Co. and has a typical repeatability of 0.15 (x+16) mg wherein x is the mean of two or more repeated test results. The TEOST test conditions are listed in Table 4. The less the amount of deposits obtained, the better the oxidation stability of the oil. The results of this test are set forth in Table 5.

TABLE 4

TEOST MHT Test Conditions

| Test Parameters | Settings |
|---|---|
| Test duration | 24 hours |
| Rod Temperature | 285° C. |
| Sample size | 8.5 g (mixture of 8.4 g of oil and 0.1 g of catalyst) |
| Sample flow rate | 0.25 g/min |
| Flow rate (dry air) | 10 mL/min |
| Catalyst | Oil soluble mixture containing Fe, Pb, and Sn |

TABLE 5

TEOST Results

| Ex./Comp. Ex. | mg deposits |
|---|---|
| Example 4 | 1.3 |
| Comp. Ex. F | 32 |

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. A reaction product of an acidic organic compound, a boron compound, and an amine, wherein the reaction product is a metal free detergent and wherein the amine is selected from the group consisting of (a) an alkoxylated amine represented by general formula:

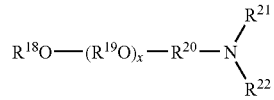

wherein $R^{18}$ is hydrogen or a substituted or unsubstituted hydrocarbyl having from 1 to about 30 carbon atoms; $R^{19}$ in each of the x ($R^{19}$O) groups is independently a straight or branched $C_2$-$C_4$ alkylene; $R^{20}$ is a bond or a substituted or unsubstituted hydrocarbylene having from 2 to about 6 carbon atoms; $R^{21}$ and $R^{22}$ are each independently hydrogen, substituted or unsubstituted hydrocarbyl having from 1 to about 30 carbon atoms, —$(R^{23})_n$—$(R^{19}O)_y R^{24}$, or $R^{21}$ and $R^{22}$ together with the nitrogen atom to which they are bonded are joined together to form a heterocyclic group; $R^{23}$ is substituted or unsubstituted hydrocarbylene containing from 1 to about 6 carbon atoms, $R^{24}$ is hydrogen or a linear or branched alkyl group having 1 to about 4 carbon atoms, n is 0 or 1, and x and y are independently an average number from 1 to about 60;

(b) an alkoxylated amine represented by general formula:

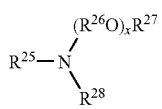

wherein $R^{25}$ is a substituted or unsubstituted hydrocarbyl having from 1 to about 30 carbon atoms and preferably from about 8 to about 30 carbon atoms; $R^{26}$ in each of the x ($R^{26}O$) groups is independently a straight or branched $C_2$-$C_4$ alkylene; $R^{27}$ is hydrogen or a straight or branched alkyl group having from 1 to about 6 carbon atoms; $R^{28}$ is a substituted or unsubstituted hydrocarbyl having from 1 to about 30 carbon atoms, and x is an average number from 1 to about 60;

(c) a dialkoxylated amine represented by general formula:

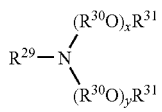

wherein $R^{29}$ is a linear or branched alkyl, linear or branched alkenyl, linear or branched alkynyl, aryl, or aralkyl group having from about 6 to about 30 carbon atoms, $R^{30}$ in each of the x ($R^{30}O$) and the y ($R^{30}O$) groups is independently a straight or branched $C_2$-$C_4$ alkylene, $R^{31}$ is independently hydrogen, or a linear or branched alkyl group having from 1 to about 4 carbon atoms and x and y are independently an average number from 1 to about 40; and mixtures thereof, wherein the acidic organic compound is selected from the group consisting of:

(A) alkyl substituted salicylic acids,
(B) di-substituted salicylic acids,
(C) oil soluble hydroxy carboxylic acids,
(D) salicylic acid calixarenes,
(E) sulfur-containing calixarenes,
(F) acids of the formula:

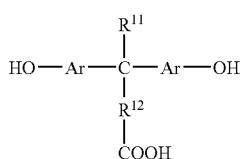

wherein $R^{11}$ is hydrocarbon or halogen, $R^{12}$ is hydrocarbon, and Ar is substituted or unsubstituted aryl, (G) acids of the formula:

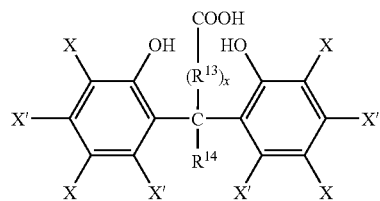

wherein X and X' are independently selected from the group consisting of hydrogen, hydrocarbyl, and halogen, $R^{13}$ is polymethylene or branched or unbranched alkylene, x is 0 or 1, and $R^{14}$ is hydrogen or hydrocarbyl, (H) acids of the formula:

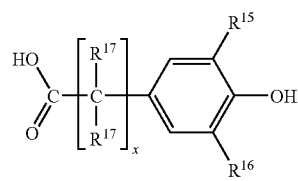

wherein
$R_{15}$ and $R_{16}$ are independently selected from the group consisting of hydrogen, hydrocarbyl groups, tertiary alkyl groups, and tertiary aralkyl groups, provided that both $R_{15}$ and $R_{16}$ are not hydrogen,
each $R_{17}$ are independently selected from the group consisting of hydrogen, hydrocarbyl groups, aralkyl groups, and cycloalkyl groups, and
x is from 0 to 24, inclusive; and
(I) salts of the foregoing acids.

2. The reaction product of claim 1, wherein the acidic organic compound is selected from the group consisting of:
(A) alkyl substituted salicylic acids, and
(B) di-substituted salicylic acids.

3. The reaction product of claim 1, wherein the boron compound is selected from the group consisting of boric acid, trialkyl borates, alkyl boric acids, dialkyl boric acids, boric oxide, boric acid complex, cycloalkyl boric acids, aryl boric acids, dicycloalkyl boric acids, diaryl boric acids, and substitution products of the foregoing with alkoxy groups, alkyl groups, and combinations thereof.

4. The reaction product of claim 1, wherein the amine is selected from the group consisting of saturated or unsaturated monoalkoxylated alkylamines, saturated or unsaturated monoalkoxylated arylamines, saturated or unsaturated polyalkoxylated alkylamines, saturated or unsaturated polyalkoxylated arylamines and mixtures thereof.

5. The reaction product of claim 1, wherein the alkoxylated amine comprises an alkoxylated derivative of a reaction product of an alkanolamine with a $C_4$-$C_{75}$ fatty acid ester.

6. The reaction product of claim 1, wherein the amine comprises an ethoxylated fatty acid amine.

7. A reaction product of an acidic organic compound, a boron compound, and an amide selected from the group consisting of monoalkoxylated amides, polyalkoxylated amides and mixtures thereof, wherein the reaction product is a metal free detergent.

8. The reaction product of claim 7, wherein the acidic organic compound is selected from the group consisting of:
(A) alkyl substituted salicylic acids,
(B) di-substituted salicylic acids,
(C) oil soluble hydroxy carboxylic acids,
(D) salicylic acid calixarenes,
(E) sulfur-containing calixarenes,
(F) acids of the formula:

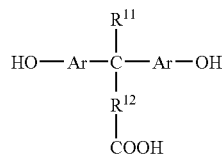

wherein $R_{11}$ is hydrocarbon or halogen, $R_{12}$ is hydrocarbon, and Ar is substituted or unsubstituted aryl,
(G) acids of the formula:

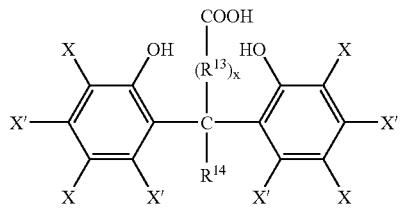

wherein X and X' are independently selected from the group consisting of hydrogen, hydrocarbyl, and halogen, $R^{13}$ is polymethylene or branched or unbranched alkylene, x is 0 or 1, and $R^{14}$ is hydrogen or hydrocarbyl,
(H) acids of the formula:

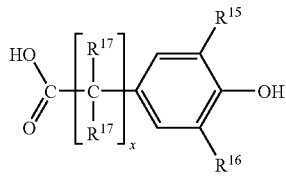

wherein
$R_{15}$ and $R_{16}$ are independently selected from the group consisting of hydrogen, hydrocarbyl groups, tertiary alkyl groups, and tertiary aralkyl groups, provided that both $R_{15}$ and $R_{16}$ are not hydrogen,
each $R_{17}$ are independently selected from the group consisting of hydrogen, hydrocarbyl groups, aralkyl groups, and cycloalkyl groups, and
x is from 0 to 24, inclusive; and
(I) salts of the foregoing acids.

9. The reaction product of claim 7, wherein the boron compound is selected from the group consisting of boric acid, trialkyl borates, alkyl boric acids, dialkyl boric acids, boric oxide, boric acid complex, cycloalkyl boric acids, aryl boric acids, dicycloalkyl boric acids, diaryl boric acids, and substitution products of the foregoing with alkoxy groups, alkyl groups, alkyl groups, and combinations thereof.

10. The reaction product of claim 7, wherein the alkoxylated amide comprises an ethoxylated fatty acid amide.

* * * * *